United States Patent [19]

Eichhorn et al.

[11] Patent Number: 5,397,846
[45] Date of Patent: Mar. 14, 1995

[54] PROCESS FOR PREPARING ORGANIC COMPOUNDS CARRYING TERT-BUTYLOXYCARBONYL GROUPS

[75] Inventors: Mathias Eichhorn, Niedernhausen; Gerhard Buhr, Koenigstein, both of Germany

[73] Assignee: Hoechst Aktiengesellschaft, Frankfurt am Main, Germany

[21] Appl. No.: 914,417

[22] Filed: Jul. 17, 1992

[30] Foreign Application Priority Data

Jul. 19, 1991 [DE] Germany .............. 41 24 029.4

[51] Int. Cl.$^6$ .............................. C08F 8/14
[52] U.S. Cl. ....................... 525/383; 525/386; 525/394; 526/264; 526/265; 526/314; 558/270
[58] Field of Search .......... 558/270; 526/314; 525/386, 383

[56] References Cited

U.S. PATENT DOCUMENTS

| | | | |
|---|---|---|---|
| 4,491,628 | 1/1985 | Ito | 430/176 |
| 4,623,705 | 11/1986 | Romano | 526/75 |
| 5,194,629 | 3/1993 | Kuehn | 548/531 |

FOREIGN PATENT DOCUMENTS

| | | |
|---|---|---|
| 0102450 | 3/1984 | European Pat. Off. . |
| 0249139 | 12/1987 | European Pat. Off. . |
| 0254853 | 2/1988 | European Pat. Off. . |
| 0404206 | 12/1990 | European Pat. Off. . |
| 0492254 | 7/1992 | European Pat. Off. . |
| 38 17 010 | 11/1989 | Germany . |

OTHER PUBLICATIONS

D. L. Flynn et al., J. Org. Chem., 1983, 48, 2424–2426. "A Convenient Method For The Preparation of 1-(tert-Butyloxycarbonyl)pyrrols"; Angewandte Chemie International Edition, Bd. 23, Nr. 4, Apr. 1984, Weinheim DE Seiten 296–297; G. Hoefle et al.

*Primary Examiner*—Fred Zitomer
*Attorney, Agent, or Firm*—Foley & Lardner

[57] ABSTRACT

The invention relates to a process for preparing organic monomeric or polymeric compounds carrying tert-butyloxycarbonyl groups, wherein a monomeric or polymeric organic compound, which possesses at least one heteroatom with an acidic proton, such as an aliphatic or aromatic alcohol, an amide, imide or lactam, is reacted with di-tert-butyl dicarbonate in an inert solvent in the presence of about 0.01 to about 10 mol percent, relative to the compound to be converted, of a catalyst at a temperature from about 0° to about 80° C. The reaction solution can be used for further processing, or the reaction product can be isolated by evaporation of the solvent or by precipitation in water and drying. The compounds are preferably used in light-sensitive coatings.

17 Claims, No Drawings

PROCESS FOR PREPARING ORGANIC COMPOUNDS CARRYING TERT-BUTYLOXYCARBONYL GROUPS

BACKGROUND OF THE INVENTION

The invention relates to a process for preparing organic monomeric or polymeric compounds carrying tert-butyloxycarbonyl (t-BOC) groups. Such compounds have diverse uses in light-sensitive coatings, such as are described, for example, in EP-A-0,102,450, EP-A-0,404,206 and EP-A-0,249,139 and DE-A 3,817,010.

Known processes for introducing the t-BOC group into monomers or polymers use compounds with heteroatoms, such as nitrogen or oxygen, to which an acidic proton is bound as starting materials. These compounds are dissolved in an inert solvent and then deprotonated by the addition of equimolar amounts of a strong base, such as potassium tert-butylate. The anion formed then is converted into the desired tert-butyloxycarbonyl group by the addition of di-tert-butyl dicarbonate which, if necessary, is dissolved in a solvent which is inert under the reaction conditions.

The disadvantages of this procedure result from the heterogeneous reaction system: since the anion formed has, as a rule, a low solubility, large quantities of solvent are required. It is also necessary to work with the exclusion of air and water, which complicates the preparation. By-products and waste products are formed, so an additional step is necessary to isolate and purify the desired products.

In EP-A-0,102,450, a preparation process is described which leads to the desired polymers with t-BOC groups by polymer-analogous reaction with the aid of phase transfer catalysis. In this process, again, the product formed must be isolated from the organic phase by precipitation.

SUMMARY OF THE INVENTION

It is therefore, the object of the present invention to provide a process which makes the desired monomers and polymers accessible in a high yield by simple means.

It is a further object of the present invention to provide a process which has wide applicability, which leads to a small amount of by-products or waste products, and which allows simple transferability to scales feasible in the industry.

It is a further object of the present invention to provide a process which, particularly in the case of the polymeric compounds, provides a reaction system such that isolation of the products is unnecessary as far as possible.

Thus, a process is provided for preparing organic monomeric or polymeric compounds carrying tert-butyloxycarbonyl groups, which comprises reacting an organic compound which possesses at least one heteroatom with an acidic proton with di-tert-butyl dicarbonate in an inert solvent in the presence of about 0.01 to about 10 mol percent, relative to the compound to be converted, of a catalyst at a temperature from about 0° to about 80° C.

The cpd. with an acidic proton has in general a pka of 5 to 25, preferably 7-20, and especially 9-18.

Further provided is a process wherein the product formed is isolated from the reaction solution by precipitation in water, filtration with suction and drying, and, if necessary, purification by reprecipitation.

Further provided is a process wherein the product formed is isolated by distilling off the inert solvent, under reduced pressure, if necessary.

These and other objects and advantages of the present invention will become apparent from the detailed description which follows.

DETAILED DESCRIPTION OF PREFERRED EMBODIMENTS

The invention relates to a process for preparing organic monomeric or polymeric compounds carrying t-BOC groups which comprises reacting an organic compound which possesses at least one heteroatom with an acidic proton with di-tert-butyl dicarbonate in an inert solvent in the presence of about 0.01 to about 10 mol percent, relative to the compound to be converted, of a catalyst at a temperature from about 0° to about 80° C.

To carry out the process according to the invention, the organic compounds used can be either polymeric or monomeric compounds which contain at least one heteroatom to which an acidic proton is bound. They are selected from the group comprising aliphatic or aromatic alcohols, amides, imides or lactams.

Examples of polymeric compounds are polyhydroxystyrene, polyhydroxymethylstyrene or poly(pyrocatechol monomethacrylate) and polymers which contain styrene, hydroxystyrene, hydroxymethylstyrene or pyrocatechol monomethacrylate as monomer units. Preferably, poly-p-hydroxystyrene, poly(pyrocatechol monomethacrylate), copolymers of pyrocatechol monomethacrylate and styrene or phenolic resins, such as the known novolaks, are used alone or as a mixture.

Examples of monomeric compounds are β-naphthol, pyrocatechol monomethacrylate, decane-1,10-diol, 2-pyrrolidone, phthalimide and succinimide, alone or as a mixture.

The monomeric or polymeric starting product is dissolved or suspended in a solvent which is inert under the reaction conditions, such as, for example, tetrahydrofuran, diethyl ether or ethyl acetate.

A catalyst is then added to the solution. The catalysts used are compounds such as tertiary amines or N,N-dialkyl-4-aminopyridines, for example diazabicyclooctane, diazabicyclononene, diazabicycloundecene, N,N-dimethyl-4-aminopyridine or pyrrolidinopyridine. Diazabicyclooctane and N,N-dimethyl-4-aminopyridine are used with particular preference. According to the invention, the catalyst used can be from about 0.1 to about 10 mol percent, preferably in the range from about 0.05 to about 2 mol percent, especially in the range from about 0.1 to about 1 mol percent, relative to the compound to be converted.

di-tert-butyl dicarbonate, dissolved in one of the above-mentioned solvents if necessary, is then added to the solution with mechanical stirring.

The reaction can be carried out at a temperature from about 0° to about 80° C., preferably from about 10° to about 50° C., particularly preferably in the range from about 20° to about 30° C.

As a rule, the reaction, preferably carried out at room temperature (from 20° to 30° C.), is complete after a few minutes up to a few hours. It is also possible to work at a higher or lower temperatures.

The progress of the reaction can readily be followed by means of a bubble counter placed on top of the apparatus. This will monitor the carbon dioxide escaping during the reaction.

The reaction solution obtained can be used directly. If necessary, the isolation of the reaction product can be effected by precipitation in water, filtration with suction, and drying. The isolation of the product can also be carried out in such a way that only the inert solvent is distilled or stripped off. This can be done under reduced pressure if necessary. Further purification can be achieved, for instance, by recrystallization, reprecipitation, distillation or chromatographic methods.

The process according to the invention leads to the desired compounds in high yield and meets all the requirements listed above. Organic compounds carrying t-BOC groups can be prepared in a simple manner and in a high yield. The reaction can take place at a temperature hardly higher than ambient, and the exclusion of air or water, hitherto necessary, can be dispensed with. Therefore, the process according to the invention can also be easily transferred to a large industrial scale.

The particular advantage of the process according to the invention is that, especially in the reaction of polymers, no product isolation is necessary: if a solvent or solvent mixture, which is suitable for the application of light-sensitive layers, is chosen as the reaction medium, the reaction solution can (if appropriate after addition of further components) be utilized directly for coating. Experience shows that the quantity of the organic catalyst does not interfere with the further processing and the reprographic properties.

The invention is described further by reference to the examples which follow, without being restricted thereto. They demonstrate the implementation of the process according to the invention.

EXAMPLE 1

10 g of commercially available poly(4-hydroxystyrene), for example MARUZEN Resin M, are dissolved in 35 ml of tetrahydrofuran, 200 mg of N,N-dimethyl-4-aminopyridine (DMAP) are added, and a solution of 20 g of di-tert-butyl dicarbonate in 15 ml of tetrahydrofuran is then added dropwise. The mixture is stirred for 1 hour at room temperature, and the product is precipitated in 1 l of water, filtered off with suction and dried in a vacuum drying cabinet at 60° C./100 mbar. This gives 17.5 g (96% of theory) of a polymer which does not show any OH band in the IR spectrum and which can be used in positive-working light-sensitive mixtures.

EXAMPLE 2

100 g of commercially available poly(4-hydroxystyrene), MARUKA Lyncur M, manufactured by Maruzen Petrochemical Co. Ltd., of hydroxyl number 455, and 200 mg of DMAP are dissolved in 400 ml of tetrahydrofuran and a solution of 50 g of di-tert-butyl dicarbonate in 100 ml of tetrahydrofuran is added dropwise with magnetic stirring. After the evolution of carbon dioxide has ceased, stirring is continued for 1 further hour. The reaction solution has a solids content of 22%. It can be stored for several months and can be used directly—after addition of a photochemical acid donor, dyes, solvents and the like—for coating pretreated aluminum supports, giving a positive-working offset printing plate.

A sample of the reaction solution was precipitated in water; the polymer obtained has a hydroxyl number of 267.

EXAMPLE 3

10 g of commercially available poly(4-hydroxystyrene), MARUKA Lyncur M, manufactured by Maruzen Petrochemical Co. Ltd., of hydroxyl number 455, and 50 mg of diazabicyclooctane (DABCO) are dissolved in 60 ml of tetrahydrofuran, and a solution of 5.45 g of di-tert-butyl dicarbonate in 10 ml of tetrahydrofuran is added dropwise to the solution under magnetic stirring. After the evolution of carbon dioxide has ceased, the product is precipitated in $H_2O$, filtered off with suction and dried at 50° C./100 mbar. This gives 11.5 g of a polymer having a hydroxyl number of 270.

EXAMPLE 4

If the DABCO in Example 3 is replaced by diazabicycloundecene (DBU), 9.25 g of a polymer having the hydroxyl number of 383 will be obtained.

EXAMPLE 5

If the DABCO in Example 3 is replaced by diazabicyclononene (DBN), 9.42 g of a polymer having the hydroxyl number of 353 will be obtained.

EXAMPLE 6

10 g of a pyrocatechol monomethacrylate/styrene copolymer (styrene content 15%; hydroxyl number 244) are dissolved in 40 ml of tetrahydrofuran, 50 mg of DMAP are added and a solution of 4.4 g of di-tert-butyl dicarbonate in 10 ml of tetrahydrofuran is added dropwise to the whole mixture with magnetic stirring. After the evolution of $CO_2$ has ceased, stirring is continued for a further 3 hours, and the product is precipitated in 1 l of water, filtered off with suction and dried at 60° C./100 mbar. Yield 11.3 g (94%); hydroxyl number 148.

EXAMPLE 7

10 g of a commercially available phenolic resin (Alnovol PN 430, HOECHST AG, hydroxyl number 434) and 50 mg of N,N-dimethyl-4-aminopyridine are dissolved in 40 ml of tetrahydrofuran with magnetic stirring, and a solution of 1.5 g of di-tert-butyl dicarbonate in 10 ml of tetrahydrofuran is then added dropwise. After 24 hours, the product is precipitated in water, filtered off with suction and dried (60° C./100 mbar). This gives 10.5 g of a polymer having a hydroxyl number of 347.

EXAMPLE 8

10 g of 2-naphthol and 50 mg of DMAP are dissolved in 25 ml of ethyl acetate. A solution of 15.1 g of di-tert-butyl dicarbonate in 20 ml of ethyl acetate is then added dropwise with magnetic stirring, the mixture is stirred for 5 hours at room temperature and the solvent is stripped off in a rotary evaporator. This gives 16.9 g (99% of theory) of 2-tert-butyloxycarbonylnaphthol as pale yellowish crystals of melting point 71°–72° C. NMR spectrum (60 MHz, $CDCl_3$): 1.6 ppm (s, 9H); 7.1–8.0 ppm (m, 7H).

EXAMPLE 9

If the DMAP in Example 8 is replaced by DABCO, 16.5 g (98% of theory) of 2-tert-butyloxycarbonylnaphthol will be obtained as pale yellowish crystals of melting point 71°–72° C.

EXAMPLE 10

5 g of pyrocatechol monomethacrylate and 50 mg of DMAP are dissolved in 20 ml of tetrahydrofuran, 6.1 g of di-tert-butyl dicarbonate in 20 ml of tetrahydrofuran are added dropwise with magnetic stirring, and stirring is continued for a further 5 hours. After stripping off the solvent, this gives 7.7 g (99% of theory) of tert-butyloxycarbonylpyrocatechol monomethacrylate as a viscous oil.

NMR spectrum (60 MHz, CDCl$_3$): 1.5 ppm (s, 9H); 2.0 ppm (s, 3H); 5.7 ppm (m, 1H); 6.3 ppm (s, 1H); 7.2 ppm (s, 4H).

EXAMPLE 11

21.8 g of di-tert-butyl dicarbonate are added to a magnetically stirred suspension of 8.5 g of decane-1,10-diol and 50 mg of DMAP in 30 ml of ethyl acetate, and the mixture is heated to the boil. After 2 hours, it is allowed to cool to room temperatures and the solvent is stripped off in a rotary evaporator. This gives 18.5 g (97% of theory) of oily 1,10-di-tert-butyloxycarbonyl-decanediol.

EXAMPLE 12

A solution of 10.9 g of di-tert-butyl dicarbonate in 10 ml of ethyl acetate is added dropwise with magnetic stirring to a solution of 3.8 ml of 2-pyrrolidone and 50 mg of DMAP in 15 ml of ethyl acetate. The mixture is stirred for 45 hours at room temperature and made up with water, the solvent is stripped off, and the residue is distilled in a bulb tube (100°/1 mm Hg). This gives 7.6 g (82% of theory) of N-tert-butyloxycarbonylpyrrolid-2-one as a colorless oil which does not show any NH band in the IR spectrum.

EXAMPLE 13

7.4 g of phthalimide and 50 mg of DMAP are suspended in 20 ml of ethyl acetate, and a solution of 11 g of di-tert-butyl dicarbonate in 15 ml of ethyl acetate is added dropwise with magnetic stirring. After 1 hour, the resulting clear solution is concentrated and the colorless solid obtained (12.3 g) is reprecipitated from methanol/H$_2$O. This gives 8.3 g (68% of theory) of N-tert-butyloxycarbonylphthalimide of melting point 90°-92° C.

EXAMPLE 14

A solution of 11 g of di-tert-butyl dicarbonate in 10 ml of ethyl acetate is added dropwise with magnetic stirring to a suspension of 5 g of succinimide and 50 mg of DMAP in 25 ml of ethyl acetate. After working up, this gives 9.3 g (93% of theory) of N-tert-butyloxycarbonylsuccinimide as a light yellow solid of melting point 76°-78° C.

Other embodiments of the invention will be apparent to those skilled in the art from a consideration of this specification or practice of the invention disclosed herein. It is intended that the specification and examples be considered exemplary only, with the true scope and spirit of the invention being indicated by the following claims.

What is claimed is:

1. A process for preparing organic monomeric or polymeric compounds bearing tert-butyloxycarbonyl groups, comprising the step of reacting (i) an organic compound which possesses at least one heteroatom with an acidic proton selected from the group consisting of aliphatic or aromatic alcohols, amides and lactams with (ii) di-tert-butyl dicarbonate in an inert solvent and in the presence of about 0.01 to about 10 mol percent, relative to the organic compounds to be converted, of a tertiary amine catalyst, at a temperature from about 0° to about 80° C.

2. The process as claimed in claim 1, wherein said organic compound is a polymer.

3. The process as claimed in claim 1, wherein said organic compound is a monomer.

4. The process as claimed in claim 1, wherein said monomeric or polymeric compound is selected from the group consisting of aliphatic alcohols, aromatic alcohols, amides, and lactams.

5. The process as claimed in claim 1, wherein said organic polymeric compound is selected from the group consisting of poly-p-hydroxystyrene, poly(-pyrocatechol monomethacrylate), copolymers of pyrocatechol monomethacrylate and styrene, phenolic resins, and mixtures thereof.

6. The process as claimed in claim 1, wherein said monomeric compound is selected from the group consisting of β-naphthol, pyrocatechol monomethacrylate, decane-1,10-diol, 2-pyrrolidone, and mixtures thereof.

7. The process as claimed in claim 1, wherein said tertiary amine is 1,4-diazabicyclo[2,2,2]octane or a 4-dialkylamino-pyridine.

8. The process as claimed in claim 1, wherein said catalyst is used in an amount from about 0.05 to about 2 mol percent, relative to the compound to be converted.

9. The process as claimed in claim 1, wherein the reaction is carried out at a temperature in the range from about 10° to about 50° C.

10. The process as claimed in claim 1, which further comprises the steps of isolating said product formed by precipitation from the reaction solution in water, filtration with suction and drying.

11. The process as claimed in claim 1, which further comprises the steps of isolating said product formed by distilling off the inert solvent, under reduced pressure, if necessary.

12. The process as claimed in claim 7, wherein said 4-dialkylamino-pyridine is 4-dimethylamino-pyridine.

13. The process as claimed in claim 1, wherein said amine catalyst is selected from the group consisting of diazabicyclooctane, diazabicyclononene, diazabicycloundecene, 4-dimethylamino-pyridine and pyrrolidinopyridine.

14. The process as claimed in claim 1, wherein the product is not isolated.

15. The process according to claim 1, wherein said at least one heteroatom with an acidic proton is selected from the group consisting of aliphatic or aromatic alcohols, amides and lactams.

16. The process according to claim 1, said process comprising the steps of
   (a) first dissolving said at least one heteroatom with an acidic proton in said inert solvent;
   (b) adding said catalyst to the solution of step (a); and
   (c) then adding said di-tert-butyl dicarbonate.

17. The process according to claim 1, wherein said at least one heteroatom with an acidic proton is selected from the group consisting of poly (4-hydroxystyrene), pyrocatechol monomethacrylate/styrene copolymer, phenolic resins, 2-naphthol, pyrocatechol monomethacrylate, decane-1,10-diol and 2-pyrrolidone.

* * * * *